United States Patent [19]

Alagy et al.

[11] Patent Number: 5,160,501
[45] Date of Patent: Nov. 3, 1992

[54] METHOD FOR THERMAL CONVERSION OF METHANE AND REACTOR FOR CARRYING OUT THE METHOD

[75] Inventors: Jacques Alagy, Charbonnieres; Paul Broutin, Ecully; Christian Busson, Charbonnieres; Jerome Weill, Lyons, all of France

[73] Assignee: Institut Francais du Petrole, Rueil-Malmaison, France

[21] Appl. No.: 700,706

[22] Filed: May 16, 1991

[30] Foreign Application Priority Data

May 17, 1990 [FR] France .................... 90 06294

[51] Int. Cl.⁵ .............................................. C07C 2/00
[52] U.S. Cl. ................................. 585/500; 585/911; 585/913; 585/924; 585/926; 585/943
[58] Field of Search .............. 585/500, 913, 924, 926, 585/943, 910, 911

[56] References Cited

U.S. PATENT DOCUMENTS

| | | | |
|---|---|---|---|
| 3,410,922 | 11/1968 | Sanchez | 585/913 |
| 4,886,932 | 12/1989 | Leyshon | 585/500 |
| 4,926,001 | 5/1990 | Alagy et al. | 585/943 |
| 4,990,714 | 2/1991 | Nemet-Mavrodin | 208/172 |
| 5,025,109 | 6/1991 | DeCaul et al. | 585/500 |

FOREIGN PATENT DOCUMENTS 0323287  7/1989  European Pat. Off. ............ 585/911

Primary Examiner—Anthony McFarlane
Attorney, Agent, or Firm—Millen, White & Zelano

[57] ABSTRACT

Method and apparatus for thermal conversion of methane to hydrocarbons of higher molecular weight, comprising a reactor 1 of elongated shape, connected at a first end to means 5 for supplying gas mixture containing methane (process gas), and connected at the opposite end to discharge means 10, the reactor having a plurality of electric heating means 3 surrounded by sheaths 4 over a first part (towards the first end). The heating means, which are substantially parallel, are arranged in sheets which are substantially parallel and perpendicular to the axis of the reactor, so that spaces or passages for circulation of the process gas and/or effluent are defined between the sheaths and/or between the sheaths and the walls 22 separating two consecutive sheets. The heating means are adapted to heat the passages by successive independent cross sections substantially perpendicular to the axis of the reactor. In a second part 8 (towards the opposite end) adjoining the first part, the reactor further comprises means 9 for cooling the effluent, connected to the means for supplying cooling fluid. The reactor also has means for introducing a gas containing hydrogen into the space surrounding the heating means inside the sheaths 4, at an appropriate pressure. The reactor and particularly the sheaths 4 are designed so that hydrogen is diffused from inside the sheaths to outside them and can then be diluted in the process gas.

14 Claims, 2 Drawing Sheets

METHOD FOR THERMAL CONVERSION OF METHANE AND REACTOR FOR CARRYING OUT THE METHOD

BACKGROUND OF THE INVENTION

The invention concerns a method for thermal conversion of methane to hydrocarbons of higher molecular weight, and the arrangement for carrying out the method. More particularly, it concerns a method for conversion or thermal cracking of methane in a reactor which has electric heating means and which enables acetylene, ethylene, benzene and a small amount of coke to be produced through dehydrogenating thermal coupling of that molecule.

All methane sources which are well known in the art may be used. A very common source of methane is natural gas. A non-exhaustive list of these sources has been provided, for example, in Applicants' European patent application EP-A-323287. In most cases the gas containing methane which is fed into the reactor contains from 1 to 90% of at least one other gas, and sometimes even more.

In European patent application EP-A-323287 Applicants have described a method for thermal conversion of methane to hydrocarbons of higher molecular weight, comprising electric heating means with heat being transferred to the gas mixture containing the methane to be converted, through the impermeable walls of ceramic sheaths which insulate said heating means from the gas mixture containing the methane. In this method the heating zone is heated through providing electricity by means of electric resistors, and the heat liberated by the Joule effect in the resistors is transmitted, chiefly by radiation, to the ceramic sheaths arranged non-contiguously around the resistors. The gas charge, which circulates substantially perpendicular to the axis of the heated sheaths, is heated essentially by convection and by radiation. In establishing this method two spaces are defined in the reactor:

firstly the reaction space or processing space, outside the sheaths protecting the resistors, in which the gas mixture containing methane circulates, secondly the resistor space, formed by the volume between the resistors proper and the insulating sheaths, into which an inert gas is preferably introduced, i.e. a gas without any methane or any hydrocarbon liable to undergo a thermal conversion reaction or any compound liable to react violently with methane or hydrogen. The gas is also chosen so that it does not damage the resistors used or accelerate the ageing of the resistors.

One of the most serious problems in thermal conversion of methane is bound up with coke formation. When too much coke is formed there is the danger of damaging the furnace before de-coking operations are carried out and, from an economic point of view, coke formation represents a serious loss in respect of both the electricity consumed and the methane consumed in forming it. This problem, which is well known in the art, is partially resolved by including hydrogen in the gas mixture containing the methane to be converted, the hydrogen representing from 1 to 90% by volume of the total volume of gas. But coke formation, chiefly on the walls of the sheaths and other high temperature surfaces in contact with the gas mixture containing methane, is not completely eradicated despite this precaution.

This explains why the following is desirable when carrying out this method for conversion of methane in an electrically heated pyrolysis oven:

to have a relatively large quantity of hydrogen in the processing zone, to have electric resistors which can deliver a large amount of energy per unit area per unit time at high temperature, to have conditions which allow for good heat transfer, so that the temperature of the heating elements, and that of the sheath surfaces in contact with the mixture of gases containing methane, is not too far above the temperature required to convert the methane.

It has been specified that, in carrying out the method, it is preferable for the resistor space to be filled with a gaseous fluid such as nitrogen, carbon dioxide gas or air. The use of air can only be considered if the sheaths form a perfect seal between the processing space and the resistor space. Otherwise there would be a serious danger of forming a very high temperature gas mixture containing oxygen, methane and hydrogen, with a consequent risk of explosion. The creation of a perfectly impermeable system is extremely difficult and also necessitates using highly impermeable and thus very high quality ceramics, that is to say, ceramics of a density close to the theoretical density, without any open pores.

Such ceramics are very expensive to use, which is a great disadvantage of the method. One therefore has to accept the use of sheaths which are not completely impermeable, and of either nitrogen or carbon dioxide. If nitrogen is used with silicon carbide resistors, there is a danger of silicon nitride forming; this is more than a negligible danger in view of the skin temperature of the resistors. In theory this has no effect on the mechanical strength of the resistors, but it changes the resistivity of the heating elements and thus accelerates their ageing, all the more since their temperature is higher and they are providing more energy. In the case of carbon dioxide, even if there is not much leakage from the resistor space to the processing space, trouble will inevitably be experienced in separating the products formed during thermal conversion of the methane: separation will be complicated a) by the presence of the carbon dioxide and b) by the presence of carbon monoxide and of water, which is inevitably formed by reaction between carbon dioxide, methane, coke and hydrogen in the processing space.

SUMMARY OF THE INVENTION

One of the objects of the invention is to avoid the disadvantages described above. The aims which it is proposed to achieve and which solve the problems raised by prior art are essentially as follows:

to limit coke formation to the maximum, particularly on hot surfaces such as the walls of the sheaths surrounding the resistors, to use, as the gas in the resistor space, a gas or a mixture of gase including one which is already present in the gas mixture circulating in the processing space, thus making it possible to use sheaths which need not be very impermeable, to improve heat exchange between the gas mixture containing methane and the hot surfaces in contact with the mixture, to increase the reliability of the arrangement.

The invention proposes a method and an arrangement for carrying it out, which provide marked improvements on prior art arrangements, such as easier, more flexible and better controlled implementation and lower cost in respect of both capital cost and functions.

More particularly, the invention concerns a method for thermal conversion of methane to hydrocarbons of higher molecular weight in an elongated reaction zone, comprising a heating zone and a cooling zone following said heating zone, wherein a gas mixture containing methane is circulated in the heating zone in a direction of flow substantially parallel to the direction (of the axis) of the elongated reaction zone, said heating zone comprising a plurality of electric heating means arranged in substantially parallel sheets which form a bundle of triangular, square or rectangular pitch in transverse elevation, said heating means being grouped in successive cross sections substantially normal to the (to the axis) of the reaction zone, the elongated sections being independent of one another and supplied with electricity so as to establish at least two parts in the heating zone, the first part enabling the charge to be brought to a temperature of no more than about 1500° C. and the second part, which follows the first, enabling the charge to be kept at a temperature substantially equal to the maximum temperature to which it was brought in said first part, and wherein the effluent from the heating zone is cooled by letting a cooling fluid into the cooling zone, whereupon said hydrocarbons of higher molecular weight are collected at the end of the reaction zone, characterized in that the electric heating means are insulated from direct contact with the gas mixture containing methane, by sheaths into which a gas containing hydrogen is fed, said sheaths having appropriate permeability and the gas being fed into said sheaths at a pressure such that at least part of the hydrogen is diffused from the inside of said sheaths to the outside, at least at certain points, whereupon the hydrogen can be diluted in the gas mixture.

The heating zone is heated by supplying electricity through heating means such as resistors; the heat liberated in the resistors by the Joule effect is transmitted, chiefly by radiation, to the sheaths arranged non-contiguously around the resistors. The sheaths are usually made of ceramics or any refractory material which will tolerate the required temperatures and reducing and oxidising atmospheres of the environment, such as some new metal alloys produced by KANTHAL SA such as KANTHAL AF, or KANTHAL APM. The gas mixture containing methane, which circulates in the heating zone substantially normal to the axis of the sheaths, is heated essentially by convection and by radiation.

Dehydrogenating thermal coupling of methane is a highly endothermic reaction, which makes it necessary to obtain very high density heat flow at a high temperature level, of the order of 1100° to 1500° C. The maximum amount of heat must be provided in the zone where the endothermic cracking and dehydrogenating reactions are carried out. Owing to the reactivity of the products formed, such as acetylene or ethylene, it is also necessary to have a controlled, relatively short contact time followed by rapid quenching, so that a "square-type" temperature profile is obtained and excessive coke formation avoided.

Heat exchange is one of the key elements for this type of very endothermic reaction, where very large quantities of energy have to be transferred from the resistors to the gas mixture containing methane, which will hereinafter be referred to as the process gas. During the preliminary study carried out by Applicants on heat exchange in a pyrolysis oven constructed according to the model used in the invention, it has been found that heat exchange from the resistor to the sheath is essentially by radiation, whereas there is virtually no exchange by radiation between the sheath and the process gas. The process gas is normally essentially a mixture of hydrogen and methane, which absorbs virtually none or very little of the radiation emitted by the sheaths. In the case envisaged in the invention therefore, heat transfer between the process gas and the sheaths is essentially transfer by convection. In such a case the quality of heat exchange will be directly related to the available exchange area and the area/volume ratio.

Thus if the exchange area is relatively small, the temperature of the sheaths will have to be increased in order to obtain a given process gas temperature corresponding to a previously chosen conversion rate. The smaller the exchange area is, the more the temperature of the sheaths will have to be increased, so there is an increased risk of coke formation and also a need to increase the temperature of the resistors. This will lead to more rapid ageing of the resistors or, if the previously chosen conversion rate is very high, the quantity of energy to be transferred may even become very large and the danger of the resistor's deteriorating may increase greatly.

The walls play an important part in heat exchange, since they can absorb the radiation emitted by the sheaths, and the temperatures of the sheaths and walls will consequently tend to balance one another. It is then possible to increase the exchange area considerably and virtually to double it by changing the design of the arrangement as follows: Whereas in the initial design the sheaths protecting the resistors and permitting heat transfer to the process gas were preferably in a staggered arrangement, according to the invention they will preferably be aligned, thus enabling n rows or sheets of m resistors to be formed in the longitudinal direction (for a total number of resistors equal to n×m), and each sheet will be separated from the next one by a wall of refractory material.

The temperature of these walls is increased by radiation and tends to reach the same level as the sheaths surrounding the resistors. So the walls will also participate in heating the process gas by convection. Thus in this embodiment, with the exchange area virtually doubled, the same process gas temperature can be obtained with a relatively lower temperature for the sheaths and walls, thereby reducing coke formation.

In this embodiment exchanges between the process gas and the walls by convection are greatly increased and may be further improved by making the gas travel at high speeds and creating turbulence zones. The increase in the gas speed may be obtained by using wall shapes which encourage such an increase and the appearance of turbulence zones. Some specially shaped walls are shown, as a non-restrictive example, in FIG. 1C.

The walls are usually made of refractory material. Any refractory material may be used to form them, some non-restrictive examples being zirconium, silicon carbide, mullite and various refractory concretes.

Since it is quite unnecessary for the walls to be impermeable, as the composition of the gas is virtually identical on each side of them, this embodiment only increases the cost of the oven minimally. On the one hand it is not necessary to have specially thick walls or a particularly complex arrangement, and on the other hand the overall dimensions of the oven are increased very little, since the width is essentially dependent on the width of the sheaths. To give an example, the sheaths may be about 150 mm wide, with a wall thickness of about 50 mm, which would only increase the overall width of the oven by about 30%.

Another advantage of this arrangement with walls is that the oven can be designed more simply, since the vertical walls support the roof of the oven as well as improving heat transfer by convection.

One of the features of the invention is that the electric resistors which supply heat to the heating zone are fed with electricity independently, either separately or in small groups, so as to define heating sections along the heating zone and thus enable the quantity of energy supplied right along that zone to be modulated.

The heating zone is normally made up of 2 to 20, preferably 5 to 12 heating sections. In the first part of the zone the gas mixture containing methane, previously heated to about 750° C., is normally brought to a temperature of no more than about 1500° C. and advantageously from 1000° to 1300° C. (the heating zone begins at the place where the charge is fed in).

The heating sections are modulated in the conventional manner; the resistance elements corresponding to the sections are generally supplied by thyristor-type modulating units. Transformers may possibly adapt the voltages a priori, while the modulators provide for precise, continuous regulation of the power input.

To enable the whole assembly to be regulated, each heating section may be provided with an insertion pyrometer with a thermocouple, adapted to the temperature level; the pyrometers are arranged in the spaces where the charge circulates, and the information is transmitted to the regulator controlling the thyristor-type modulator.

In the first part of the heating zone electricity is used almost exclusively to bring the reaction mixture from its initial temperature (for example about 750° C.) to the temperature at which the endothermic reactions of dehydrogenating coupling of methane take place (for example about 1200° C.). Thus the maximum energy has to be supplied to the reaction medium at the beginning of the second part of the heating zone; this is easily done by modulating one or more heating sections.

The length of the first part of the heating zone is usually from 20 to 80% and advantageously from 30 to 70% of the total length of the zone.

The electricity supplied to this first part of the heating zone is such that it generates a marked temperature gradient, usually from about 0.5° to about 25° C./cm and advantageously from about 1° to about 20° C./cm.

In the second part of the heating zone the electricity supplied to the various heating sections of the zone is modulated so that the temperature variation right along the zone is small, normally less than about 50° C. (+ or −25° C. above or below the index value) and advantageously less than about 20° C.

Furthermore, the use of various independent heating cross sections makes it possible to provide the maximum heating energy at the place where the majority of endothermic reactions take place, in the second part of the heating zone, and to maintain a quasi-uniform temperature in the rest of the heating zone.

The length of the heating zone is usually from about 50 to about 90% of the total length of the reaction zone.

A very strong heat flow is obtained at a high temperature level, particularly under the heating conditions described above. This usually implies a special choice of material for the resistors: apart from being resistant to the reducing atmosphere under the operating temperature conditions, it must be able to deliver a relatively strong potential per unit area. An example of material suitable for making the resistors is molybdenum bisilicide ($MoSi_2$). Heating elements made of molybdenum bisilicide have many advantages when used at high temperature:

they can accept a strong load (power emitted per unit area) of up to 20 $W/cm^2$, they can operate at very high temperature, they show negligible ageing with the passage of time, they can easily tolerate reducing atmospheres at high temperatures.

In the method of the invention the heating zone is followed by a cooling (or quenching) zone, so that the temperature of the effluent from the heating zone is brought down very quickly, for example, to about 300° C.

In one embodiment direct quenching is carried out; the effluent from the reaction leaves the heating zone and is cooled very rapidly by putting it into direct contact with a cooling fluid, which is injected into the effluent by means of at least one injector, usually made of ceramics, at the periphery of the reactor. The cooling fluid may be liquefied petroleum gases, propane, hydrocarbon oils or water. Propane is the preferred quenching gas, since it can also be partially cracked and thus contribute to the formation of products such as ethylene. The total effluent resulting from the mixture is then collected and separated.

In a preferred embodiment the reaction effluent from the heating zone is cooled by putting it into indirect contact with a cooling fluid, for example by circulating the fluid in sealed pipes within the cooling zone.

With these features taken together, the method results in thermal conversion of methane to acetylene, ethylene and benzene products, with a good conversion rate and high selectivity for these products.

Hydrocarbon charges which can be used in the invention are charges which are gaseous under normal conditions of temperature and pressure, usually containing at least 10% by volume of methane, for example from 10 to 99%, more frequently from 20 to 99% and preferably from 30 to 80%. As specified above, the rest of the charge in nearly all cases includes a proportion of hydrogen usually ranging from 1 to 90% by volume. It may also include other gases, such as saturated or unsaturated aliphatic hydrocarbons, comprising a number of atoms equal to 2 or more, such as ethylene, ethane, propane or propylene. It may also comprise nitrogen, carbon dioxide or carbon monoxide.

Diluting water vapour may be added to the charges defined above, without going beyond the scope of the invention; the weight ratio of diluting water vapour to the hydrocarbon charge is generally of the order of 0.1:1 to 1:1.

The charges to be treated usually have a dwell time of about 2 milliseconds to about 1 second, and preferably from about 30 to about 400 milliseconds, in the reaction zone.

The gas containing hydrogen, which is let into the sheaths surrounding the resistors, may be substantially pure hydrogen, industrial hydrogen or a mixture of hydrogen with another inert gas, for example nitrogen, helium, argon, water vapour or carbon dioxide. It is preferable to use pure or industrial hydrogen or a mixture of helium and hydrogen, or a mixture of argon and hydrogen, or a mixture of water vapour and hydrogen usually containing at least 5% and preferably at least 10% by volume of hydrogen. When a mixture of nitrogen and hydrogen is used it usually contains at least 25 and preferably at least 50% by volume of hydrogen.

The sheaths must be permeable enough to enable at least part of the hydrogen contained in the gas let into the resistor space to be diffused to the process space, at least at some points. If the permeability of the sheaths were such that all the gaseous compounds contained in the gas let into the resistance space could be diffused to the process space, this would not be outside the scope of the invention. The permeability may result from the deliberate provision of an imperfect seal on each sheath and/or from making the sheaths of a material with open pores giving passage to hydrogen, in other words, making them of a material permeable to hydrogen. It is usually recommended to use a permeable material.

Thus in a prefered embodiment of the invention the sheaths, which insulate the electric heating means from direct contact with the gas mixture containing methane, are made of a porous material with sufficient porosity to allow hydrogen to be diffused through them. The sheaths are thus preferably made of a porous ceramic material, with at least about 1%, at the most 40% and usually from about 5 to 30% by volume open porosity relative to the volume of the wall.

The use of substantially pure hydrogen, which is at least partly diffused to the processing space, has several advantages. It does not complicate separating processes downstream of the pyrolysis oven, since the gas to be cracked is usually a mixture of methane or natural gas and hydrogen, with the hydrogen preferably in a proportion of 10 to 80% and usually 30 to 70% by volume.

The introduction of hydrogen right along the pyrolysis oven reduces the overall size of the oven. If one aims to obtain a certain proportion of hydrogen in the cracked gas at the outlet, the proportion at the inlet of the oven will be less and, if the dwell time has to be kept the same, the reaction volume and hence the size of the oven will be smaller. This arrangement will also bring an increasing proportion of hydrogen along the pyrolysis oven, which is an advantage from the point of view of the kinetics of cracking and the stability of the product: too much hydrogen at the beginning of the oven would inhibit the cracking reactions too much, but at the end of the oven, when a considerable quantity of products have formed, particularly ethylene and acetylene, it is advantageous to have more hydrogen so as to avoid coke formation. So the desired effect can be obtained from the hydrogen which enters the processing zone at the level where each seal is provided (at least 1 per sheath) on each sheath protecting the resistors, and/or which is diffused through the walls of the sheaths.

Further according to the invention, since it is no longer desirable to have the most perfect possible seals between the processing space and the resistor space, the cost of the oven and also the thermomechanical strains at the sheath connections are reduced, thus making the whole arrangement more reliable.

Another advantage is the available choice in respect of the resistor-protecting sheaths which separate the processing space from the resistor space. As has been mentioned several times, when nitrogen or $CO_2$ is used as the sealing gas the consumption of that gas, i.e. the leakage of that gas from the resistor space into the processing space, has to be limited for many reasons. It has been seen that this is done by seeking to obtain maximum gas tightness, particularly where the sheaths are joined to the rest of the oven. It is also done by using sheaths made of ceramics, particularly silicon carbide, which are as gas-tight as possible, i.e. very high grade and hence very expensive.

It is well known in the art that there are many varieties of ceramics, particularly silicon carbide, produced from very different powder qualities and under very different sintering conditions. But without going into detail it may be noted that one of the quality criteria is in connection with the lower residual porosity after sintering. It is well known that, if part of the porosity is closed, i.e. with no effect on the overall impermeability of the material, another part—a more than negilible proportion particularly with the latest silicon carbide—has open porosity, and particularly that hydrogen is diffused through that material at high temperature. So it will be appreciated that when a gas such as nitrogen or $CO_2$ is used as the sealing gas, very high quality silicon carbide has to be used, of a density close to the theoretical density and thus virtually without any open pores, a) in order to avoid having the gas escape from the resistor zone to the processing space and b) since the difference in the partial pressure of hydrogen is positive in the processing-resistor direction, in order to avoid having the hydrogen contained in the processing gas diffused into the resistor space.

In the invention on the other hand, what was a crippling disadvantage becomes a decisive advantage.

Thus the use of sheaths made of average quality ceramics, particularly silicon carbide, with at least about 1% by volume (e.g. about 20% by volume) open porosity is thus not only possible but even desirable, a fact which lowers the cost of producing the oven. In addition, the very existence of the open porosity creates a partial pressure of hydrogen at the surface of the ceramic sheath towards the processing space, and this so to speak insulates the surface of the ceramics from the processing gas. Without wishing to be tied to any particular theory, this explains the marked reduction in coke formation, since coke normally forms essentially on the surface of the sheaths, whereas now the products formed will be in a local atmosphere which is richer in hydrogen and hence less favourable to coke formation.

In this specification "open porosity" designates porosity made up of microcavities included in the solid ceramic pieces in question, the adjective "open" signifying that there is free passage a) between most of the microcavities and b) between the microcavities and the inner and outer surfaces of the pieces in question. The idea of free passage must also be considered according to the nature of the environment and the physical conditions to which the ceramic is subjected. Free passage will be easy, particularly for small molecules such as hydrogen or helium, especially if there is a pressure difference between the two surfaces of the ceramic piece. In this case the piece is described as permeable, e.g. to hydrogen, or not gas-tight.

"Closed porosity" refers in this specification to porosity formed by microcavities which do not communicate with the surface of the piece. In this case the closed porosity only produces an overall reduction in the density of the piece.

The invention also relates to the arrangement for carrying out the method. The arrangement may equally be used to carry out other endothermic reactions which normally take place at temperatures above about 600°

C., for example from about 700° to about 1450° C., with dwell times of the order of 2 milliseconds to 1 second.

More particularly, the invention concerns an arrangement for carrying out the method, comprising a reactor 1 of elongated shape along one axis, preferably of square or rectangular cross section, comprising means for supplying with gas mixture at a first end, means for discharging the effluent produced at the opposite end, and means for supplying with cooling fluid between the two ends, said reactor comprising in a first part (towards the first end) a plurality of electric heating means 3 surrounded by sheaths 4, said means being substantially parallel and arranged in substantially parallel sheets perpendicular to the axis of the reactor, so as to define spaces or passages for the circulation of the gas mixtures and/or effluent between the sheaths and/or the sheets formed by the sheaths, said heating means and said sheaths being adapted to heat said passages by successive independent cross sections substantially normal to the axis of the reactor; said reactor further comprising heat control and heat modulating means connected to said heating means, and comprising in the second part 8 (towards the opposite end) adjoining the first part, means 9 for cooling effluent, connected to said means for supplying cooling fluid, characterised in that it comprises means for letting a gas containing hydrogen into the sheaths 4 at an appropriate pressure, and that said sheaths have sufficient permeability to enable at least part of the hydrogen to be diffused from the inside of said sheaths to the outside, at least at certain points, the hydrogen then being diluted in the gas mixture.

The means for feeding the gas in at an appropriate pressure are known in the art. They may also comprise means for regulating and controlling pressures which obtain inside and outside the sheaths.

The cooling means are means adapted to cool the effluent from the first zone, through direct or indirect contact.

The sheaths which surround the resistors, usually non-contiguosly, may be in a superposed or staggered arrangement and may form a bundle of triangular or square pitch in transverse elevation.

The total number of sheets of heating means and the number of heating means per sheet are not a decisive feature of the method; they will obviously depend on the dimensions, the heating means, the sheaths surrounding them, and the walls (if any) separating the sheaths. The heating elements may be identical or different, both in dimensions and heating power.

The number of heating elements determines the maximum electric power available for a given reaction volume and also affects the dwell time of the charge; it should be chosen according to the permissible throughput of charge, taking these parameters into account.

In accordance with the invention the whole reactor—the heating zone and quenching zone—may either be made in one piece or made by juxtaposing and joining various elements of the same shape and assembling them by any suitable means such as straps or flanges. The electric heating means which can be used in the invention are preferably heating resistors suitable for use up to temperatures of the order of 1500° C. in a totally reducing atmosphere; resistors made of molybdenum bisilicide are preferable, for example pin shaped resistors.

The sheaths which surround the resistors so as to avoid direct contact between the gas mixtures of the charge and the resistors are preferably of tubular shape. The sheaths of refractory material are usually made of ceramics. Ceramics such as mullite, cordierite, silicon nitride, silicon carbide, silica or alumina may be employed; silicon carbide is preferable since it has good heat conductivity. In cases where the sheaths are separated by walls, the material chosen for the walls may be the same as that used for the sheaths but it is often different, particularly because of the cost of producing the oven.

The distance between the heating elements and the sheaths depends on the cross section of the heating element. For heating means where the maximum diameter of the circle containing them equals d, the sheaths normally used are tubular or cylindrical with a diameter D normally from about $1.2 \times d$ to about $8 \times d$, and usually from about $1.5 \times d$ to about $4 \times d$.

The heating elements are disposed in substantially parallel sheets perpendicular to the direction of flow of the charge (the process gas), and are preferably substantially aligned, so that the distance between two adjacent sheaths is as small as possible, allowing for the permissible loss of pressure requirements. The distance between the sheaths in two adjacent sheets, or between the sheaths of one sheet and the nearest wall in cases where the sheets are separated by walls, is usually the same as the distance between two consecutive sheaths in a given sheet. This distance will generally be such that the passages formed between the sheaths or between the sheaths and the nearest wall, in which passages the gas mixture containing methane circulates, will have a dimension from about 1 to about 100 mm and most frequently from about 5 to about 40 mm.

In one embodiment of the invention the empty spaces or passages defined above, designed for circulation of the process gas, are at least partly occupied by linings, which are usually made of ceramics and preferably heat conducting. For a given type of reactor the dwell time of the charge in the reactor can thus be shortened, while homogenising the flow of the gas mixture and improving the distribution of dissipated heat. The linings may be in various forms, for example in the form of rings (Raschig, Lessing or Pall), saddles (Berl saddles), rods or closed cylindrical tubes.

The invention will be understood better from the following description of some embodiments, given as non-restrictive examples and referring to the accompanying drawings, in which similar members are designated by the same reference numbers and letters.

DETAILED DESCRIPTION OF THE DRAWINGS

Figure 1A:
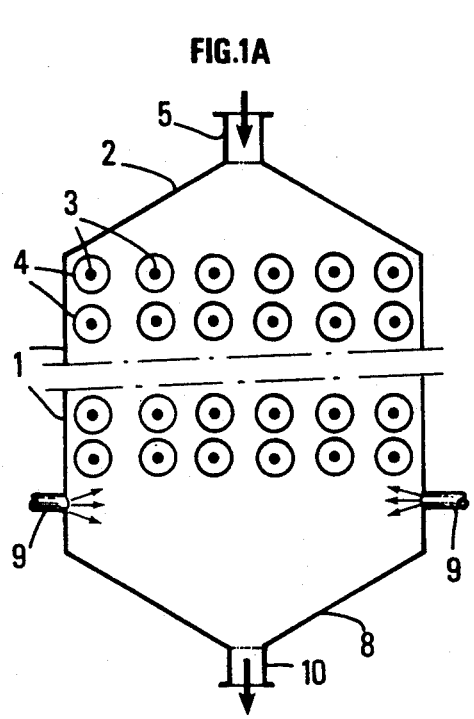
FIGS. 1A, and 1B and 1C are longitudinal sections through a reactor in a plane perpendicular to the axis of the sheaths. In the case of FIG. 1B the reactor contains a lining. In the case of FIG. 1C it has walls separating successive sheets of sheaths.

FIG. 1A shows an embodiment of a vertical reactor 1 of elongated shape and rectangular cross section, comprising a distributor 2 which enables the reactor to be supplied with gaseous reaction mixture through an inlet orifice 5. The reaction mixture, containing e.g. 50% of methane, has been pre-heated in a conventional pre-heating zone (not shown), preferably by convection. The reactor has a plurality of electrical heating means 3 surrounded by sheaths 4, which are arranged in parallel sheets and form a bundle of square pitch in one plane (the plane of the figure). These sheets define heating cross sections substantially perpendicular to the axis of the reactor, defined in the direction of flow of the charge.

Figure 1B:
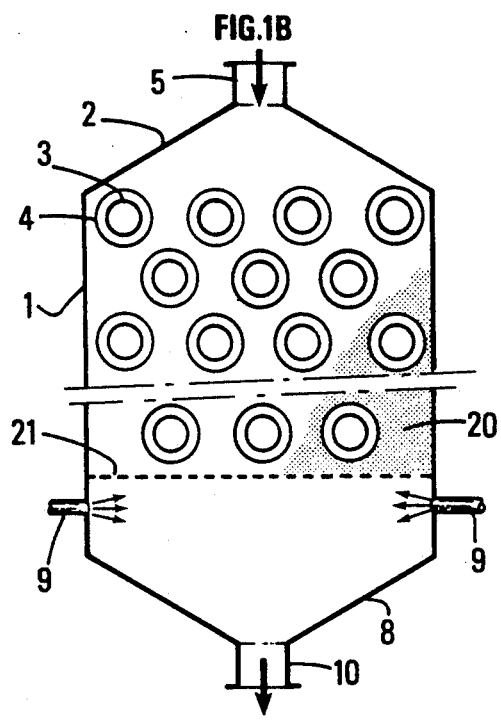
Figure 1C:
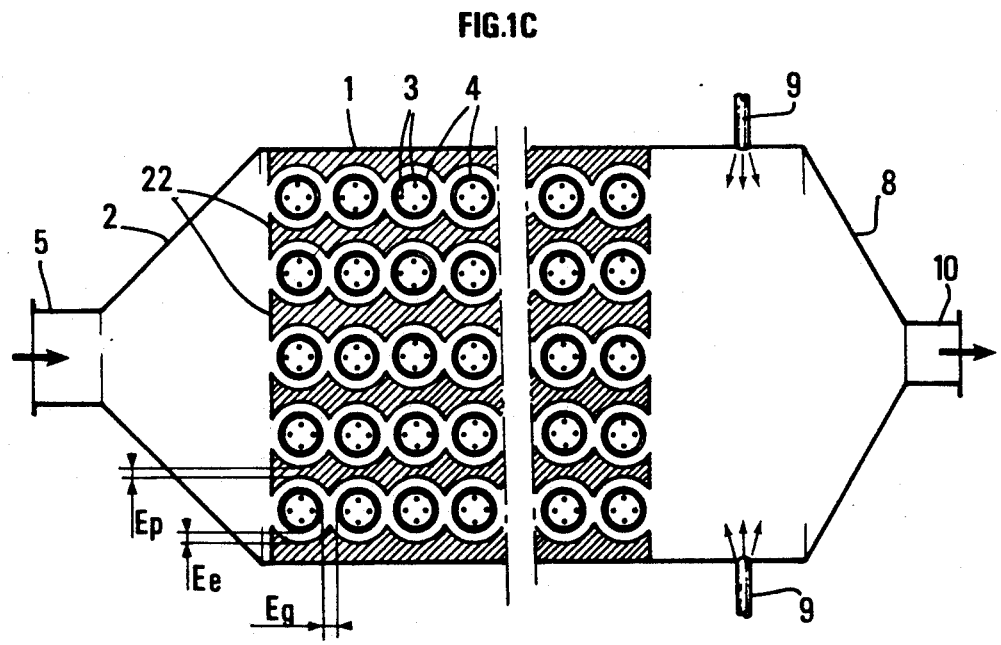
Figure 1D:
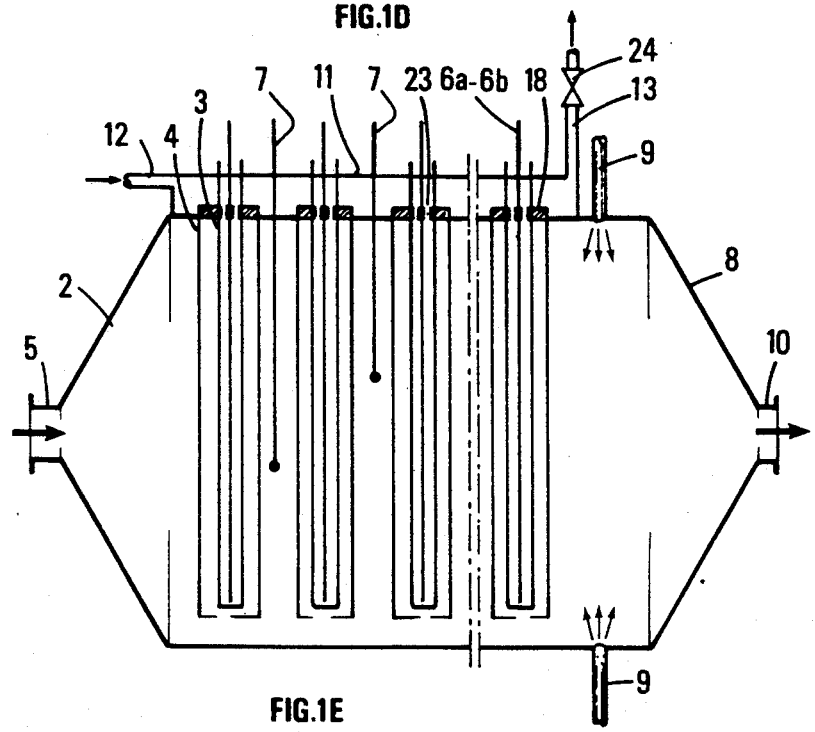
FIGS. 1D and 1E are longitudinal sections through a reactor along the axis of the sheaths.
Figure 1E:
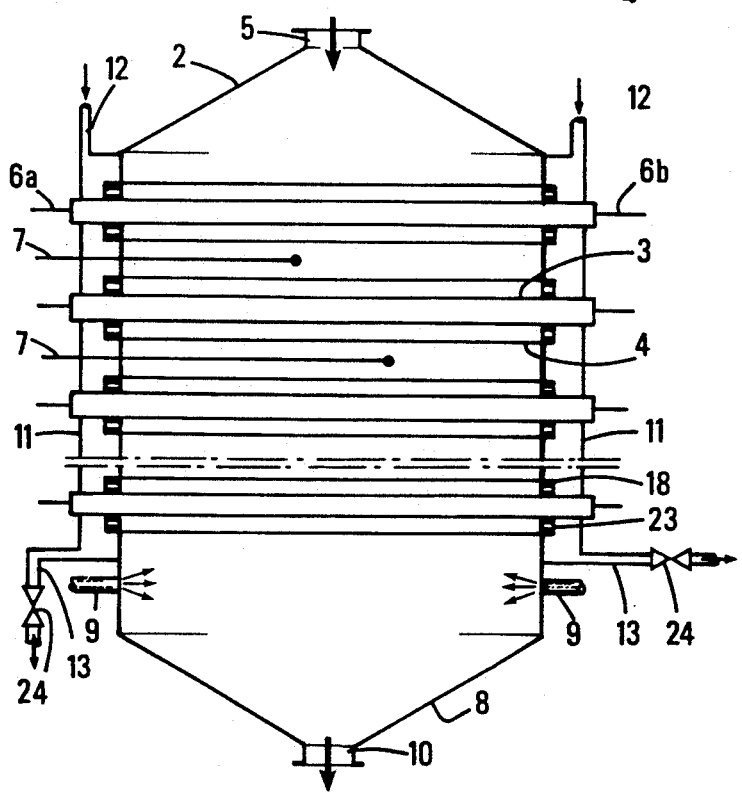

The heating sections are independently supplied with electricity by a pair of electrodes (6a, 6b in FIGS. 1D and 1E). Thermocouple pyrometric probes (7 in FIGS. 1D and 1E) are contained in the spaces where the charge passes between the sheaths 4. They enable the temperature of each heating section to be regulated automatically by a conventional regulating and modulating device (not shown).

In the first part of the heating zone the sheaths are heated so that the temperature of the charge passes rapidly from 750° C. (pre-heating temperature) to about 1200° C. This gradual heating zone generally makes up about 65% of the total length of the heating zone. The gas mixture then circulates in the second part of the heating zone, where the temperature is generally kept at a constant level substantially equal to that reached at the end of the first heating zone, generally about 1200° C. This is done by modulating the electrical power supplied to a plurality of heating sections which make up the second part of the heating zone. In this way the temperature variation is no more than about 10° C. above or below the index value. The length of the second heating zone is about 35% of the total heating zone.

On leaving the heating zone the effluent from the reaction is cooled in a cooling zone 8. It is put into contact with a quenching agent such as propane which is fed in through quenching injectors 9, arranged at the periphery of the reactor 1 and connected to an external propane source (not shown). All the effluent gases are cooled to a temperature of about 500° C. and collected through an outlet orifice 10 at the end of the reaction zone 1.

In another embodiment (not shown) the effluent may be cooled by making it circulate through impermeable pipes arranged in zone 8 through which the quenching agent flows, the pipes being connected to the outside source of quenching agent.

In the FIG. 1B embodiment the reactor, which is identical with that shown diagrammatically in FIG. 1A, has a lining 20 in the space where the charge circulates. The lining is advantageously made of ceramics and held by a grid 21 at the end of the heating zone. The sheaths 4 are arranged in parallel sheets and form a bundle with a triangular pitch (staggered arrangement) in one plane (the plane of the figure).

FIG. 1C shows an embodiment of a horizontal reactor 1 of elongated shape and rectangular cross section. The only difference from the reactor shown in FIG. 1A is the fact that it is substantially horizontal, that it has sheaths arranged in parallel sheets, forming a bundle with a square pitch in one plane (the plane of the figure), and that the sheets are separated by walls 22 advantageously made of ceramics. The walls have a shape adapted to create turbulence, with cells at the level of each sheath 4.

FIG. 1D shows the same components as FIG. 1A has, for a horizontal reactor: it also shows a protective casing 11 including an orifice 12 through which the gas containing hydrogen is let in, and an orifice 13 fitted with a valve 24 for regulating the flow of gas containing hydrogen. The casing 11 is fixed on the metal reinforcement of the reactor 1 and surrounds all the electric resistors and sheaths containing them, except for the end of the resistors through which electricity is supplied. The resistors 3 are pin shaped and are positioned in the sheaths by rings 18, made e.g. of ceramic fibre, containing passages 23 which enable the gas containing hydrogen to enter the space between the resistors and the sheaths.

FIG. 1E shows the same components as have been described in connection with FIG. 1A. It also shows the protective casings 11 provided with orifices 12 and 13 which enable the gas containing hydrogen to circulate in the casings; the gas enters the resistor space through the orifices 23 of the rings 18 for positioning the resistors. The orifices 13 are fitted with valves 24 to make it easier to regulate the flow of the gas containing hydrogen. The casings 11 are fixed on the metal reinforcement of the reactor and surround the set of electric resistors and sheaths containing them, except for the end of the resistors through which electricity is supplied. The gas containing hydrogen is usually circulated at a pressure slightly higher than that of the process gas in the reactor, thereby providing a perfectly controlled atmosphere and better diffusion of the hydrogen contained in the gas to the processing space.

The pressure could be virtually equal to that of the process gas, in which case, as in the case of a global excess pressure, it is usually preferable for the partial pressure of the hydrogen to be slightly higher in the resistor space than in the processing space, so as to be sure that the hydrogen will diffuse well from the resistor space to the processing space. The difference between the partial pressures of the hydrogen will generally be such that the pressure in the gas contained in the resistor space is at least 0.1% and preferably at least 1% higher than that of the hydrogen contained in the process gas. The difference in absolute pressure between the resistor space and the processing space, or the excess pressure, will preferably be such that the pressure in the resistor space is at least 0.1% and usually at least 1% higher than the pressure in the processing space. It is not necessary to have very great excess pressure, and the pressure in the resistor space will generally be less than twice that in the processing space.

Figure 2:
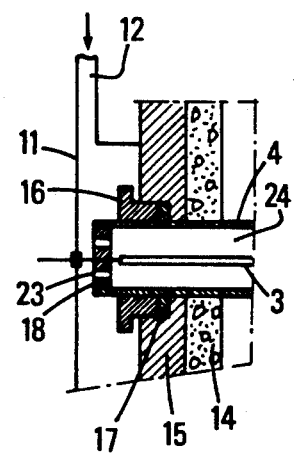
FIG. 2 illustrates a detail of the heating zone in the same plane as that in FIGS. 1B and 1E.

FIG. 2 shows a detail of an embodiment of the heating zone according to the invention. Resistors 3 of cylindrical shape are used as electrical heating means. The resistors have cold zones at each end and part of the central zone, which is the hot zone, representing e.g. about 68% of the total length (sic).

A reactor of rectangular cross section is made, the walls being made of insulating refractory concrete 14 and a metallic reinforcement 15. A circular hole is formed in two opposed side walls, into which is passed a sheath 4, made for example of ceramics, with a diameter twice that of the electric resistor 3. The sheath 4 is positioned by means of a gland system 16 acting on a covering of refractory material 17, e.g. a covering of ceramic material, in a groove at the level of the metallic reinforcement. The resistor 3 is positioned in the sheath 4 by means of rings 18 made, for example, of ceramic fibre; the rings contain orifices 23 which enable the gas containing hydrogen, which is let into the casing 3 through the pipe 12, to enter the resistor space 24.

The hot zone of the resistor 3 is positioned so that it does not enter the orifice passing through the wall of insulating concrete. It is not essential to use a covering 17 at the level of the gland, since the gland acts as a positioning means in the invention and the provision of the tightest possible seal between the inside and outside of the reactor is not its primary purpose. The glands may advantageously be replaced by a simpler means for positioning the sheaths, such as simple rings of refractory material.

Thus a number of sheathed heating resistors are arranged in the walls, e.g. of ceramic material, in successive horizontal rows which are preferably aligned to form a bundle of square or rectangular pitch on the side walls of the furnace. A casing 11, with only the ends of the resistors and/or their electrical supply 6 extending outside it, has a stream of gas containing hydrogen passing through it.

EXAMPLE 1

A horizontal, indirect quenching reactor is used, with a total length of 6.1 m and a rectangular cross section of 1.4×3.2 m. The means for heating the reactor are pin shaped electric resistors of the trade mark KANTHAL, made of molybdenum bisilicide ($MoSi_2$) of the SUPER-KANTHAL type; the resistors are surrounded by ceramic sheaths arranged concentrically with the circle containing them.

The sheaths are made of silicon carbide produced by NORTON; they are of the KRYSTON type with 15% by volume open porosity. Each sheath is closed at one end and surrounds two pin shaped resistors (FIG. 1D). The sheaths are arranged normal to the direction in which the charge circulates (vertically), in parallel sheets, and forms a bundle of square pitch in perpendicular elevation. The length of each branch of the pin of the electric resistor is 1.4 m and the diameter of the resistor is 9 mm. The ceramic sheaths have a length of 1.4 m, an outside diameter of 150 mm and an inside diameter of 130 mm; the distance between adjacent sheaths is 10 mm.

The first part of the heating zone, 3.7 m long, comprises 23 sheets of resistors, each sheet having 20 sheaths; in this zone the charge, which is pre-heated to 800° C., is brought to 1200° C. The heating of the zone is regulated by thermocouples arranged in the spaces where the charge circulates.

The second part of the heating zone, adjacent to the first part, is 2.4 m long; it is made up of 15 sheets of 20 sheaths, arranged in the same way as in the first part. This zone comprises 5 heating sections which are regulated independently, enabling the temperature therein to be kept at 1200° C. plus or minus 10° C.

The effluent gases are cooled to 800° C. at the first stage, by indirect exchange with the gases of the charge; other heat exchanges then bring the temperature down to about 300° C.

The charge used comprises methane diluted with hydrogen in a volume ratio of 1:1. The mixture is preheated to 800° C. and cracked in the reactor described above. The absolute pressure of the gas mixture in the reactor is kept substantially constant at 0.125 MPa. Substantially pure hydrogen is let into the resistor space, so that a substantially constant absolute pressure of 0.130 MPa is obtained and maintained therein.

When the mixture has been cooled to room temperature, the following quantities of the main products are obtained per 200 moles of an equal-volume mixture of methane and hydrogen:

| PRODUCTS | QUANTITIES |
| --- | --- |
| $H_2$ | 143 moles |
| $CH_4$ | 70 moles |
| $C_2H_2$ | 6 moles |
| $C_2H_4$ | 4 moles |
| Benzene | 0.75 moles |
| Coke | 54 g |

EXAMPLE 2

A horizontal, indirect quenching reactor is used, with a total length of 4.3 m and a rectangular cross section of 1.4×3.7 m. The means for heating the reactor are pin shaped electric resistors of the trade mark KANTHAL, made of molybdenum bisilicide ($MoSi_2$) of the SUPER-KANTHAL type; the resistors are surrounded by ceramic sheaths arranged concentrically with the circle containing the resistors.

The sheaths are made of silicon carbide produced by NORTON; they are of the KRYSTON type with an open porosity of 15% by volume. Each sheath is closed at one end and surrounds two pin shaped resistors (FIGS. 1C and 1D). The sheaths are arranged normal to the direction in which the charge circulates (vertically), in parallel sheets, and form a bundle of square pitch in perpendicular elevation. The length of each branch of the pin of the electric resistor is 1.4 m and the diameter of the resistor is 9 mm. The ceramic sheaths have a length of 1.4 m, an outside diameter of 150 mm and an inside diameter of 130 mm; the distance e.g. (FIG. 1C) between two adjacent sheaths is 20 mm. The sheets of sheaths are separated by a wall of refractory concrete based on electrofused alumina. The distance Ee (FIG. 1C) between the sheaths and the wall, or the dimension of the passages, is 10 mm. The walls have a thickness Ep (FIG. 1C) of 15 mm in their thinnest part. The reactor thus has 25 sheets of 20 sheaths and 19 walls.

The first part of the heating zone, 1.7 m long, comprises 10 sheets of resistors, each sheet having 20 sheaths; in this zone the charge, which is pre-heated to 1000° C., is brought to 1200° C. The heating of this zone is regulated by thermocouples arranged in the spaces where the charge circulates.

The second part of the heating zone, adjacent to the first part, is 2.55 m long; it is made up of 15 sheets of 20 sheaths, arranged in the same way as in the first part. This zone comprises 3 heating sections which are regulated independently, enabling the temperature therein to be kept at 1200° C. plus or minus 10° C.

The effluent gases are cooled to 800° C. at a first stage by indirect exchange with the gases of the charge; other heat exchanges then enable the temperature to be brought down to about 300° C.

Methane diluted with hydrogen in a volume ratio of 1:1 is used as the charge. The mixture is pre-heated to 1000° C. and cracked in the reactor described above. The absolute pressure of the mixture of gases in the reactor is kept substantially constant at 0.125 MPa. Substantially pure hydrogen is let into the resistor space, so that a substantially constant absolute pressure of 0.130 MPa can be obtained and maintained therein.

When the mixture has been cooled to room temperature, the following quantities of the main products are obtained per 200 moles of an equal-volume mixture of methane and hydrogen:

| PRODUCTS | QUANTITIES |
| --- | --- |
| $H_2$ | 142.5 moles |
| $CH_4$ | 70 moles |
| $C_2H_2$ | 6.3 moles |
| $C_2H_4$ | 4 moles |
| Benzene | 0.74 moles |
| Coke | 48 g |

We claim:

1. In a method of thermal conversion of methane to hydrocarbons of higher molecular weight in an elongated reaction zone, comprising a heating zone and a cooling zone following said heating zone, said method comprising circulating a charge comprising a gas mixture containing methane in the heating zone in a direction of flow substantially parallel to the axis of the elongated reaction zone, said heating zone comprising a plurality of electric heating means arranged in substantially parallel sheets which form a bundle of triangular, square or rectangular pitch in transverse elevation, said heating means being grouped in successive cross sections substantially normal to the direction of the reaction zone, the sections being independent of one another and supplied with electricity so as to establish at least two parts in the heating zone, the first part enabling the charge to be brought to a maximum temperature of above about 750° C. to no more than about 1500° C. and the second part, which follows the first, enabling the charge to be maintained at a temperature substantially equal to said maximum temperature, and cooling effluent from the heating zone by introducing a cooling fluid into the cooling zone and collecting said hydrocarbons of higher molecular weight at the end of the reaction zone, the improvement wherein the electric heating means are insulated from direct contact with the gas mixture containing methane by sheaths into which a gas containing hydrogen is fed, said sheaths having sufficient permeability and said gas fed into said sheaths being at a sufficient pressure, such that at least part of the hydrogen is diffused from the inside of said sheaths to at least selected locations on the outside of said sheaths.

2. The method of claim 1, wherein a first part of the heating zone is heated to a maximum temperature of about 1500° C. so as to form a heat gradient of about 0.5° C./cm to about 25° C./cm over a length of about 20 to about 80% of the total length of the heating zone, and wherein the second part, following the first part, is heated so that the variation in temperature right along the second part of the heating zone is less than about 50° C.

3. The method of claim 1, wherein the pressure of the gas in the sheaths is at least 0.1% higher than the pressure outside them.

4. The method of claim 1, wherein the sheaths insulating the electric heating means from direct contact with the gas mixture containing methane are made of a porous material, with sufficient porosity to enable hydrogen to be diffused through said sheaths.

5. The method of claim 4, wherein the sheaths are made of porous ceramic material with a porosity of a minimum of about 1% and a maximum of about 40% by volume.

6. The method of claim 1, wherein the heating means are insulated from direct contact with the gas mixture containing methane by cylindrical sheaths, the diameter of which is from about 1.2 to about 4 times the maximum diameter of the circle containing said heating means.

7. The method of claim 1, wherein the dimension of the passages in which the gas mixture containing methane flows is from about 1 to about 100 mm.

8. The method of claim 1, wherein each sheet is separated from the next one by a wall of refractory material.

9. The method of claim 1, wherein the electric heating means comprise resistors made of molybdenum bisilicide.

10. A method according to claim 1, wherein in the first part of the heating zone, the charge is brought to a temperature of 1000°–1300° C.

11. A method according to claim 2, wherein in the first part of the heating zone, the charge is brought to a temperature of 1000°–1300° C.

12. The method of claim 10, wherein the sheaths insulating the electric heating means from direct contact with the gas mixture containing methane are made of a porous material, with sufficient porosity to enable hydrogen to be diffused through said sheaths.

13. A method according to claim 2, wherein the variation in temperature right along the second part of the heating zone is less than about 20° C.

14. A method according to claim 11, wherein the variation in temperature right along the second part of the heating zone is less than about 20° C.

* * * * *